(12) United States Patent
Dirauf et al.

(10) Patent No.: US 10,813,603 B2
(45) Date of Patent: Oct. 27, 2020

(54) COUCH PANEL AND PATIENT COUCH FOR MEDICAL IMAGING METHODS

(71) Applicants: Franz Dirauf, Ebensfeld (DE);
Michael Grasruck, Nuremberg (DE);
Alexander Krämer, Irchenrieth (DE);
Riccardo Kunze, Erlangen (DE); Otto Sembritzki, Wachenroth (DE)

(72) Inventors: Franz Dirauf, Ebensfeld (DE);
Michael Grasruck, Nuremberg (DE);
Alexander Krämer, Irchenrieth (DE);
Riccardo Kunze, Erlangen (DE); Otto Sembritzki, Wachenroth (DE)

(73) Assignee: Siemens Aktiengesellschaft, Munich (DE)

( * ) Notice: Subject to any disclaimer, the term of this patent is extended or adjusted under 35 U.S.C. 154(b) by 260 days.

(21) Appl. No.: 14/882,566

(22) Filed: Oct. 14, 2015

(65) Prior Publication Data

US 2016/0120487 A1 May 5, 2016

(30) Foreign Application Priority Data

Oct. 29, 2014 (DE) .................. 10 2014 222 061

(51) Int. Cl.
*A61B 6/04* (2006.01)

(52) U.S. Cl.
CPC .......... *A61B 6/0442* (2013.01); *A61B 6/0487* (2020.08); *A61B 6/0407* (2013.01); *A61G 2210/50* (2013.01)

(58) Field of Classification Search
CPC ... A61B 6/0442; A61B 6/0457; A61B 6/0407; A61G 2210/50
See application file for complete search history.

(56) References Cited

U.S. PATENT DOCUMENTS 3,778,049 A * 12/1973 Viamonte, Jr. ...... A61B 6/0428
378/209
3,783,863 A * 1/1974 Kliever ............... A61B 6/0421
128/847

(Continued)

FOREIGN PATENT DOCUMENTS

CN 1960780 A 5/2007
CN 101715309 A 5/2010

(Continued)

OTHER PUBLICATIONS

Enyclopedia of Physics, Joseph Rosen, Ph. D, Facts on FIle, Inc, p. 223 (Year: 2004).*

(Continued)

*Primary Examiner* — David R Hare
*Assistant Examiner* — Alexis Felix Lopez
(74) *Attorney, Agent, or Firm* — Lempia Summerfield Katz LLC

(57) ABSTRACT

A couch panel for a patient couch for a medical imaging method is disclosed. The couch panel is of single-shell design, beads are formed in the longitudinal direction of the couch panel, wherein the number and the shape of the beads are chosen such that the couch panel has a predefinable geometric moment of inertia. The two longitudinally extending edges of the couch panel are bent upward. This is advantageous because of the cost-effective production of a couch panel and, in the case of X-ray imaging, in the low radiation absorption. A patient couch having a couch panel of this kind is likewise disclosed.

12 Claims, 5 Drawing Sheets

(56) References Cited

U.S. PATENT DOCUMENTS

| | | | | |
|---|---|---|---|---|
| 3,835,482 | A * | 9/1974 | Tersch | A47C 1/14 4/573.1 |
| 3,848,132 | A * | 11/1974 | Foderaro | A61B 6/0428 378/209 |
| 4,034,224 | A * | 7/1977 | Heavens | A61B 6/0428 378/20 |
| 4,145,612 | A * | 3/1979 | Cooper | A61B 6/0442 378/208 |
| 4,146,793 | A * | 3/1979 | Bergstrom | A61B 6/0428 378/161 |
| 4,234,978 | A * | 11/1980 | Snow | A47C 17/64 297/239 |
| 4,252,594 | A * | 2/1981 | Cooper | A61B 6/0442 156/285 |
| 4,584,729 | A * | 4/1986 | Roberts | A61G 1/01 5/625 |
| 4,688,780 | A * | 8/1987 | Hanz | A61B 6/0421 5/601 |
| 5,034,970 | A * | 7/1991 | Yahata | A61B 6/035 378/15 |
| 5,054,049 | A * | 10/1991 | Manabe | A61B 6/032 378/20 |
| 5,068,935 | A * | 12/1991 | Hagopian | A61G 7/0507 4/584 |
| 5,131,105 | A * | 7/1992 | Harrawood | A61G 13/02 5/607 |
| 5,230,112 | A * | 7/1993 | Harrawood | A61G 13/02 5/607 |
| 5,303,438 | A * | 4/1994 | Walker | A47D 15/008 5/110 |
| D355,988 | S * | 3/1995 | Brooking | D6/349 |
| 5,473,784 | A * | 12/1995 | Nixon | A61B 6/0442 5/601 |
| 5,808,468 | A * | 9/1998 | Bis | A61B 5/0555 324/318 |
| 6,003,174 | A * | 12/1999 | Kantrowitz | A61B 6/0442 5/601 |
| 6,345,114 | B1 * | 2/2002 | Mackie | A61N 5/1048 378/65 |
| 6,769,145 | B1 * | 8/2004 | Pfeuffer | A61B 6/0442 378/209 |
| 6,954,952 | B1 * | 10/2005 | Kroupa | A61G 1/00 378/209 |
| 7,017,209 | B1 * | 3/2006 | De Jong | A61B 6/0442 378/20 |
| 7,024,710 | B2 * | 4/2006 | Izuhara | A61B 6/04 108/145 |
| 7,676,255 | B2 * | 3/2010 | Wang | A61B 6/04 5/600 |
| 7,753,587 | B2 * | 7/2010 | Kusch | A61B 6/0442 378/209 |
| 8,220,085 | B2 * | 7/2012 | Claffy | A47C 19/202 5/110 |
| 9,433,349 | B2 * | 9/2016 | Emaci | G01R 33/3415 |
| 2002/0027969 | A1 * | 3/2002 | Maida | A61B 6/0442 378/20 |
| 2002/0170116 | A1 * | 11/2002 | Borders | A61B 6/0457 5/600 |
| 2004/0001571 | A1 * | 1/2004 | Jahrling | A61B 6/032 378/209 |
| 2004/0034932 | A1 * | 2/2004 | Zacharopoulos | A61B 6/04 5/601 |
| 2004/0143905 | A1 * | 7/2004 | Pastyr | A61B 6/0407 5/601 |
| 2006/0002511 | A1 * | 1/2006 | Miller | A61N 5/107 378/65 |
| 2006/0241408 | A1 * | 10/2006 | Yakubovsky | A61B 6/032 600/429 |
| 2007/0050908 | A1 * | 3/2007 | Kogan | A61B 6/0457 5/128 |
| 2007/0074347 | A1 * | 4/2007 | Coppens | A61B 6/0442 5/600 |
| 2007/0124858 | A1 * | 6/2007 | Ahlman | A61B 6/0442 5/81.1 R |
| 2007/0164230 | A1 | 7/2007 | Rigney et al. | |
| 2008/0005844 | A1 * | 1/2008 | Tybinkowski | A61B 6/032 5/661 |
| 2009/0308400 | A1 * | 12/2009 | Wilson | A61F 5/3769 128/845 |
| 2011/0107515 | A1 * | 5/2011 | Brunker | A61B 6/0442 5/601 |
| 2012/0159711 | A1 * | 6/2012 | Boersma | A61B 5/0555 5/600 |
| 2013/0096417 | A1 | 4/2013 | Hering | |
| 2014/0016740 | A1 * | 1/2014 | Gotman | A61B 6/032 378/20 |
| 2015/0026889 | A1 * | 1/2015 | Roselius | A61B 6/0442 5/601 |
| 2016/0174914 | A1 * | 6/2016 | Lerch | A61B 6/0407 5/601 |
| 2016/0242708 | A1 * | 8/2016 | Kaiser | A61G 13/101 |
| 2017/0079590 | A1 * | 3/2017 | Batzer | A61B 6/0407 |
| 2017/0119277 | A1 * | 5/2017 | Wu | A61B 6/03 |
| 2018/0008211 | A1 * | 1/2018 | Shang | B29C 70/46 |

FOREIGN PATENT DOCUMENTS

| | | |
|---|---|---|
| CN | 103142227 A | 6/2013 |
| CN | 202960546 U | 6/2013 |
| CN | 1442117 A | 9/2013 |
| DE | 2204283 A1 | 9/1972 |
| DE | 2602954 A1 | 7/1977 |
| DE | 3808321 A1 | 9/1989 |
| DE | 102012019119 A1 | 1/2013 |
| DE | 102012000772 A1 | 7/2013 |
| DE | 102014216497 A1 | 11/2015 |

OTHER PUBLICATIONS

Chinese Office Action for Chinese Application No. 201510713632.7, dated Jan. 29, 2018.
German Office action for related German Application No. 10 2014 222 061.0, dated Oct. 21, 2015, with English Translation.
Chinese Office Action for Chinese Application No. 201510713632.7 dated Nov. 13, 2018.

* cited by examiner

COUCH PANEL AND PATIENT COUCH FOR MEDICAL IMAGING METHODS

This application claims the benefit of DE 10 2014 222 061.0, filed on Oct. 29, 2014, which is hereby incorporated by reference in its entirety.

TECHNICAL FIELD

The embodiments relate to a couch panel for a patient couch for use in medical imaging methods and to a patient couch having such a couch panel.

BACKGROUND

Patient couches serve to support an examination object, (e.g., a human or animal body or a material sample), during imaging with an imaging device. FIGS. 1 to 3 are schematic views depicting a patient couch 1, or parts thereof, according to the prior art. Patient couches of this kind are used, for example, in a computed tomography apparatus 4 (CT apparatus).

The patient couch in FIG. 1, also referred to as a patient table, has a couch panel 6 on which the examination object 3, here a patient, is supported. The head of the examination object 3 is supported on a head shell 5. The couch panel 6 is arranged on a pedestal 7 and may be driven, (e.g., by a motor), in a linear movement into a gantry aperture 8 of the CT apparatus 4. After being driven out, a protruding part 9 of the couch panel 6 is not supported by the pedestal 7. The couch panel 6 for a patient couch 1 has a high load-bearing capacity and stiffness in order to hold the examination object 3 in a steady and stationary position, even when the examination object 3 is located in the gantry of the CT apparatus 4 or of a magnetic resonance tomograph.

Moreover, during X-ray imaging, the couch panel 6 does not appreciably attenuate the X-rays used for the imaging procedure, and the couch panel 6 does not cause any disruptive image artifacts. The couch panel 6 for CT patient couches 1 may therefore be made of a carbon fiber-reinforced plastic (CFRP). The CFRP material forms a box-like structure that is filled with a foamed plastic.

As is depicted in FIG. 2, threaded inserts 10 are integrated in the couch panel 6 at the structurally reinforced end directed away from the head shell 5 of the couch panel 6, by which threaded inserts 10 the couch panel 6 is screwed onto a movable linear carriage 11, as is depicted in FIG. 3. The unsupported end of the couch panel 6, (e.g., the protruding part 9), is driven together with the examination object 3 into the gantry of the CT apparatus 4 by the movement of the linear carriage 11 on running tracks 12, so that slice images may be taken in the apparatus. At the front end of the couch panel 6, a shaped plastic component may be let into the CFRP structure and serves to secure the head shell 5 or a phantom carrier.

A couch panel 6 of this kind according to the prior art is described in the post-published document DE 10 2014 216 497 A1. The known structure of the couch panel 6 is tried and tested and permits imaging of good quality. A disadvantage, however, is the relatively complicated and expensive production, which may include the following acts: (1) production of a foam core of homogeneous density, (2) generally by profile milling, (3) positioning of reinforcements and metal threads, (4) insertion of a shaped piece for receiving head shell or phantom carrier, (5) application of a CFRP laminate, and (6) hardening of the CFRP matrix.

SUMMARY AND DESCRIPTION

The scope of the present invention is defined solely by the appended claims and is not affected to any degree by the statements within this summary. The present embodiments may obviate one or more of the drawbacks or limitations in the related art.

The object of the present embodiments is to provide, for a patient couch, a couch panel that may be produced more cost-effectively and more easily than known couch panels and that nonetheless has the required geometric moment of inertia. Moreover, when used for X-ray imaging, the absorption by the couch panel may be as low as possible, so that the radiation exposure of a patient remains low. A further object is to make available an associated patient couch.

A single-shell couch panel, also referred to as table panel, has a plurality of beads formed in the longitudinal direction of the couch panel. The couch panel serves to support an examination object on a patient table during a medical imaging method. The couch panel is curved concavely in the transverse direction. Beads are manually or mechanically produced, groove-shaped depressions in, for example, sheet metal plates, cylinders, tubes or similar objects. Beads serve to increase the stiffness of individual parts or structures. Moreover, the two longitudinal edges of the couch panel are bent up, (e.g., drawn upward), in order to further increase the geometric moment of inertia.

In certain embodiments, a couch panel for a patient couch for a medical imaging method is provided. The couch panel is of a single-shell design, has beads formed in the longitudinal direction of the couch panel, wherein the number and the shape of the beads are chosen such that the couch panel has a predefinable geometric moment of inertia. The two longitudinally extending edges of the couch panel are bent upward.

An advantage of the embodiments lies in producing couch panels in a single-shell design with a thin wall. The production costs may be greatly reduced compared to the known couch panels with a two-shell design with foam insert.

By virtue of the optimized shaping, however, a sufficient load-bearing capacity and stiffness is still achieved for use in X-ray imaging methods, without adversely affecting the quality of the imaging.

In one development, the couch panel may be curved concavely in the transverse direction. It is thereby configured to the shape of an examination object and has increased stability.

In a further embodiment, the couch panel may be made from a fiber-reinforced plastic, (e.g., CFRP). Light, stable, and radioparent couch panels may be produced in this way. The radiation exposure of the patient is reduced as a result of the high level of radioparency of the couch panel.

In a further embodiment, the wall thickness of the couch panel may measure 2 to 5 mm.

In one development, a reinforcement may be provided in the couch panel and locally increases the geometric moment of inertia. The reinforcement may be formed in those areas where the greatest load is exerted by an examination object.

In certain embodiments, a patient couch for a medical imaging method with a couch panel is provided. The patient couch has a pedestal and a linear carriage arranged movably on the pedestal and on which the couch panel is secured.

In one development, an accessory holding unit may be arranged on one end of the couch panel and is fixed in the beads by holding rods of the accessory holding unit or is configured to the profile of the couch panel.

Moreover, the patient couch may have rollers, which are arranged and designed to guide and support the couch panel on the beads during movement of the couch panel in the longitudinal direction.

DETAILED DESCRIPTION

Figure 1:
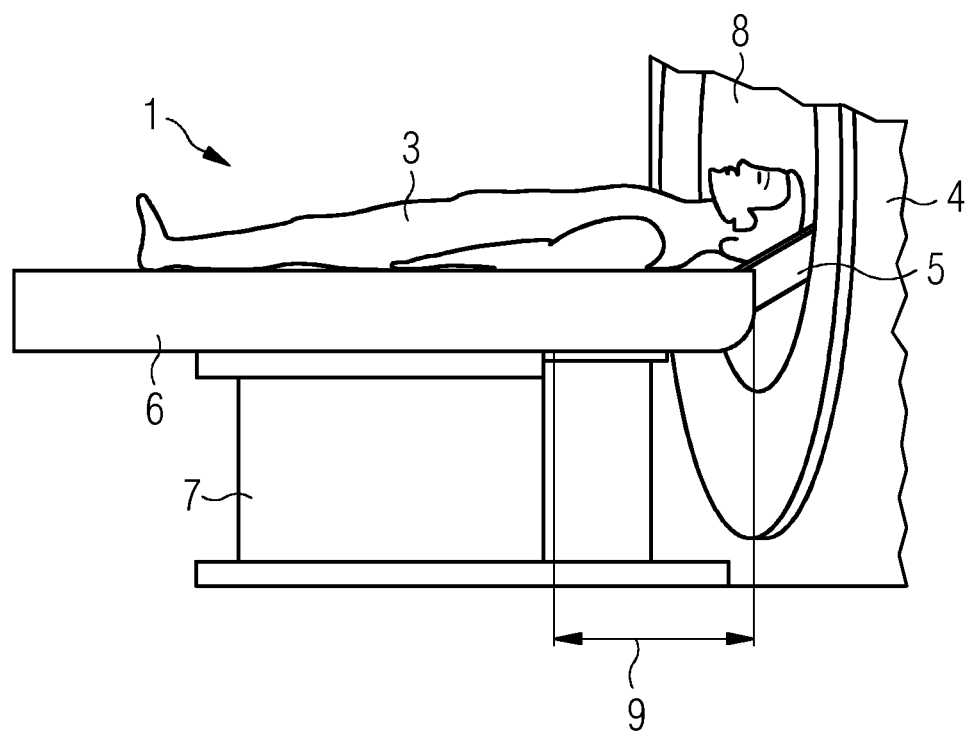
FIG. 1 depicts a side view of a patient couch according to the prior art.
Figure 2:
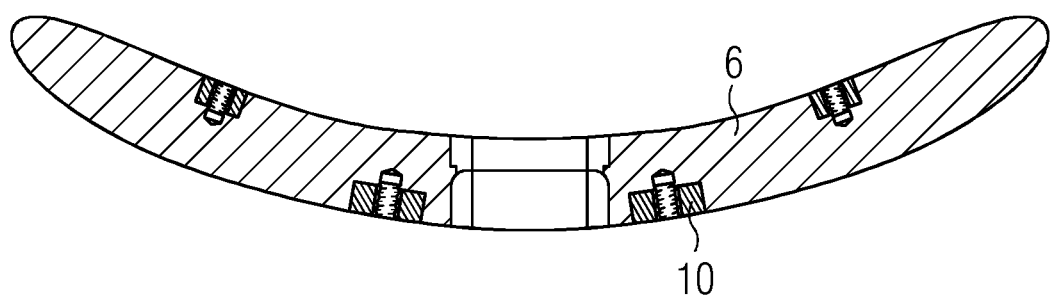
FIG. 2 depicts a cross section of a couch panel according to the prior art.
Figure 3:
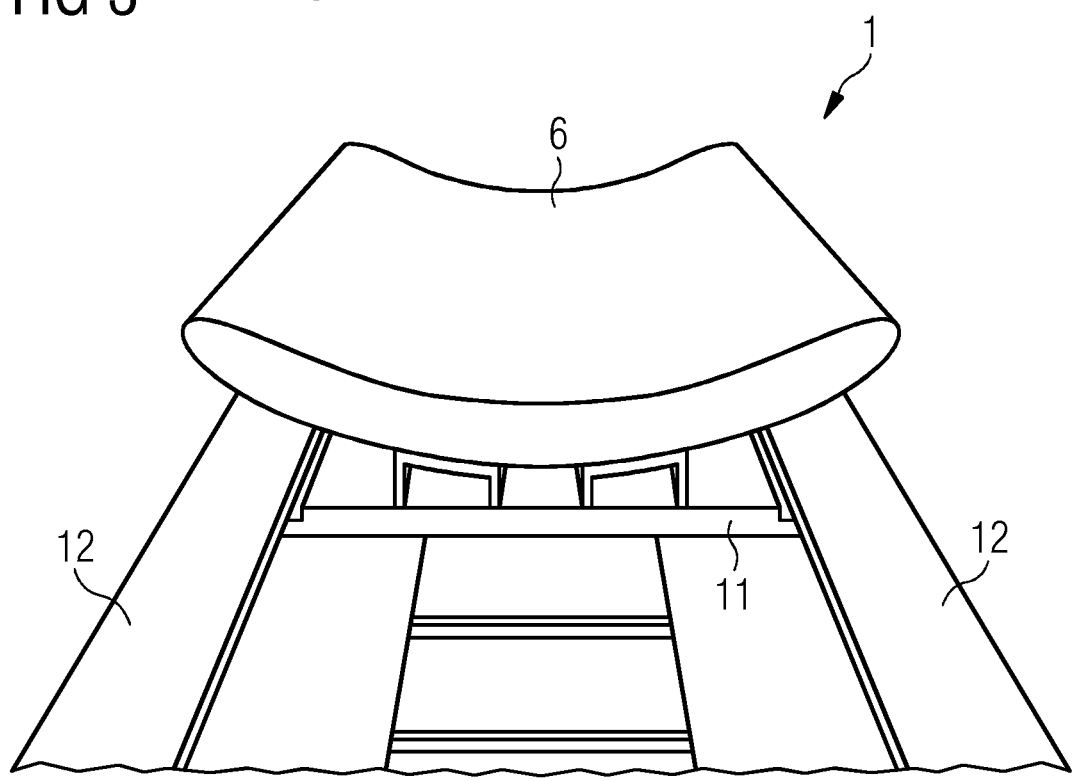
FIG. 3 depicts an oblique view of a couch panel on a linear carriage according to the prior art.
Figure 4:
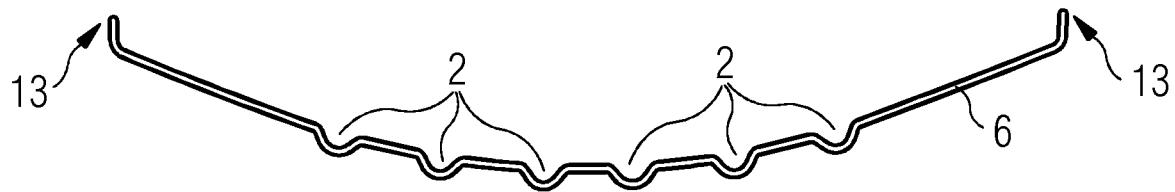
FIG. 4 depicts an example of a cross section through a single-shell couch panel.

FIG. 4 depicts a cross section through a single-shell couch panel 6 with beads 2 formed therein. The beads 2 are arranged substantially in the area in which an examination object lies. The beads may be formed regularly, and may be in a semicircular shape, and are approximately 1 cm in depth and 2.5 cm in width. The two edges 13 of the couch panel 6 in the longitudinal direction are bent up and point more or less vertically upward. The upwardly protruding part of the edges 13 is approximately 3 cm high. The couch panel 6 has a length of approximately 210 cm and a width of approximately 50 cm.

The material of the couch panel 6 is a carbon fiber-reinforced plastic (CFRP) or another fiber composite. The number and shape of the beads and the upward bending of the edges 13 are chosen in such a way as to obtain a predefinable geometric moment of inertia, for example 2 to 3 times greater than a single-curve couch panel. This provides that no undesirable bending and deformation of the couch panel 6 takes place when the couch panel 6 is subjected to a load by an examination object.

Figure 5:
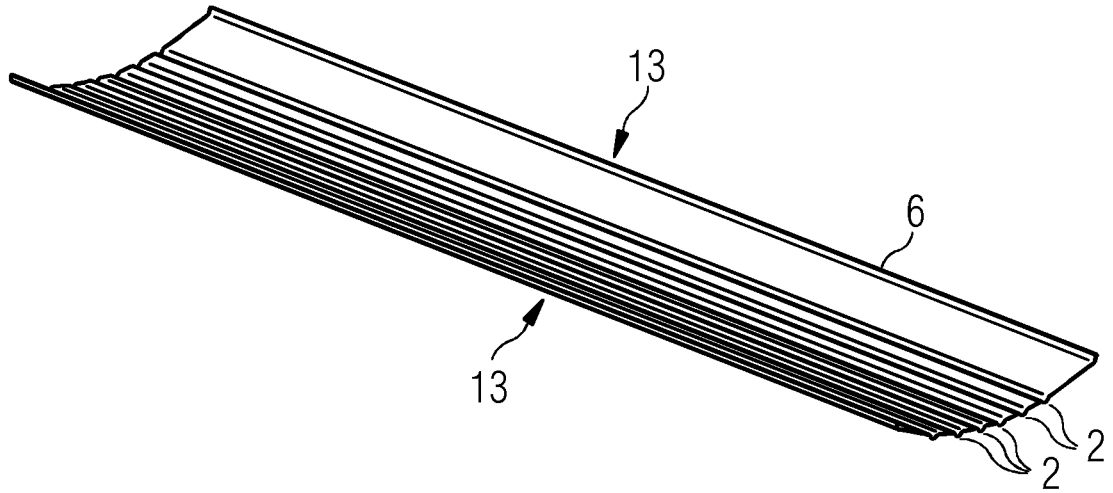
FIG. 5 depicts an example of an oblique view of a single-shell couch panel.

FIG. 5 depicts a perspective view of the couch panel 6 according to FIG. 4. The beads 2, formed in the longitudinal direction of the couch panel 6, and the upwardly bent edges 13 may once again be seen.

Figure 6:
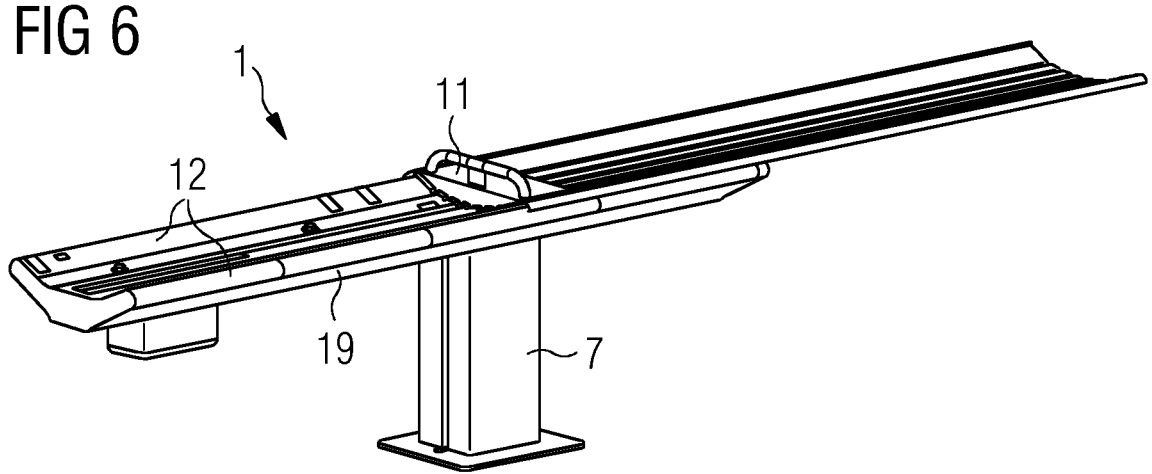
FIG. 6 depicts an example of an oblique view of a patient couch having a single-shell couch panel.

FIG. 6 depicts a perspective view of a patient couch 1 for a CT examination with the couch panel 6 according to FIG. 4 and FIG. 5. The couch panel 6 is secured on a movable linear carriage 11, as a result of which an examination object located on the couch panel 6 may be pushed into the gantry of a CT apparatus. The linear carriage 11 runs on running tracks 12, which are arranged in a table top 19. The table top 19 is located on a pedestal 7.

Figure 7:
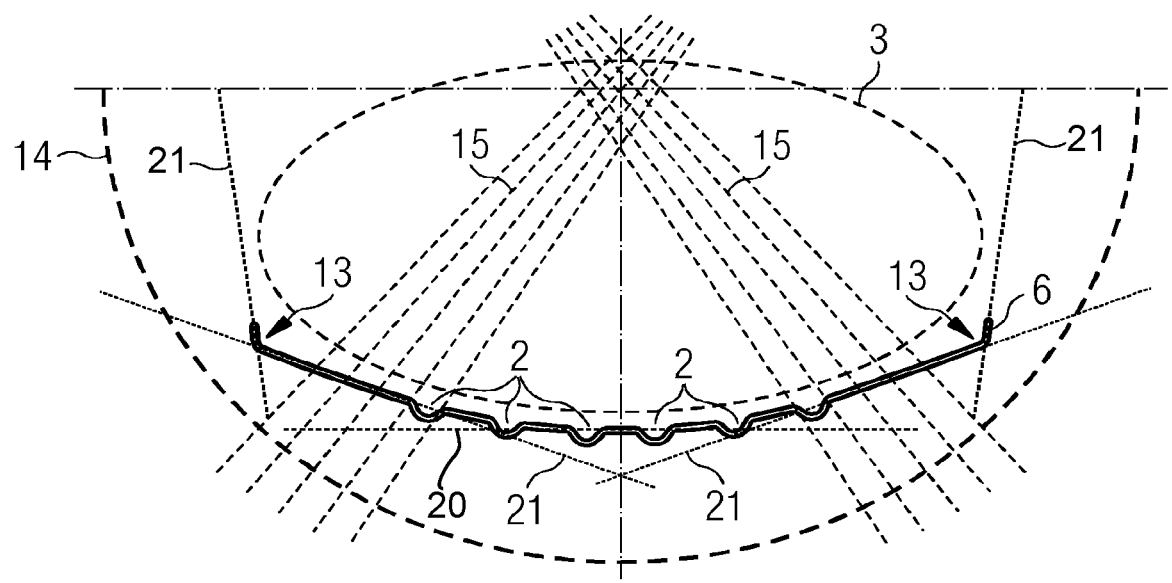
FIG. 7 depicts an example of a sectional view through a single-shell couch panel in a CT gantry.

FIG. 7 depicts a sectional view through the single-shell couch panel 6 according to FIG. 4 to FIG. 6, wherein it is pushed into a gantry aperture 14 of a CT apparatus. The X-rays 15 pass through the examination object 3, for example a patient, before passing through the couch panel 6.

Artifacts in the imaging of the examination object 3 are avoided by the rounded shape of the beads 2, since the surfaces whose first tangents 20 are oriented in the direction of the examination object 3 are only very small.

Similarly, the configuration and in particular the orientation of the upwardly bent edges 13 are such that the second tangents 21 of the edges 13 do not point in the direction of the imaging volume (e.g., examination object 3). Artifacts in the 3D imaging are likewise avoided in this way.

Figure 8:
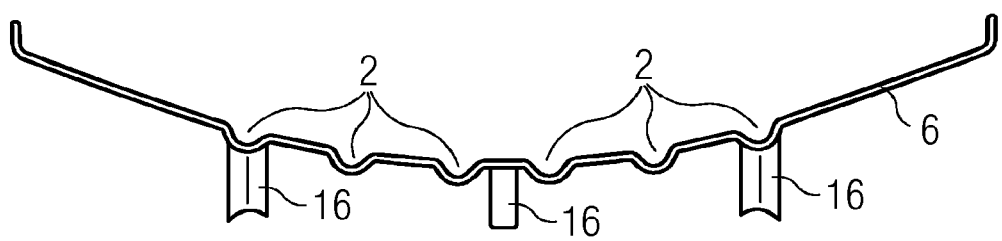
FIG. 8 depicts an example a sectional view of a single-shell couch panel on rollers.

FIG. 8 depicts a cross section through a couch panel 6 with beads 2, wherein the beads 2 in the profile of the couch panel 6 serve as longitudinal guides for the rollers 16 of a patient couch. The rollers 16 support the couch panel 6.

Figure 9:
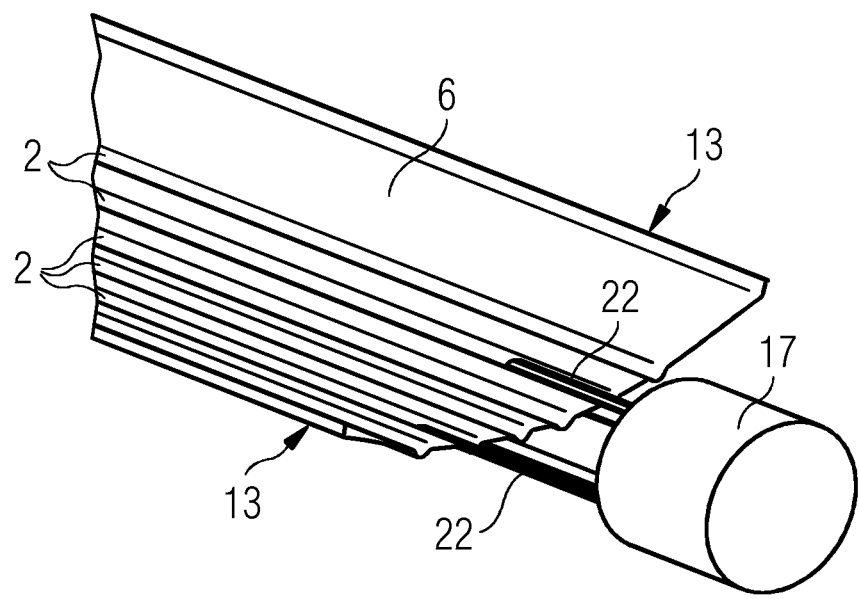
FIG. 9 depicts an example of a partial view of a single-shell couch panel with an accessory holding unit.

FIG. 9 depicts a partial view of a couch panel 6 with beads 2 and with upwardly bent edges 13, wherein an accessory holding unit 17 is mounted on the end of the couch panel 6. The accessory holding unit 17 for this purpose has holding rods 22 that may be pushed at the front end onto the couch panel 6. On the top face of the couch panel 6, the holding rods 22 are guided in the beads 2. The accessory unit 17 may, for example, receive a head support or a phantom.

Figure 10:
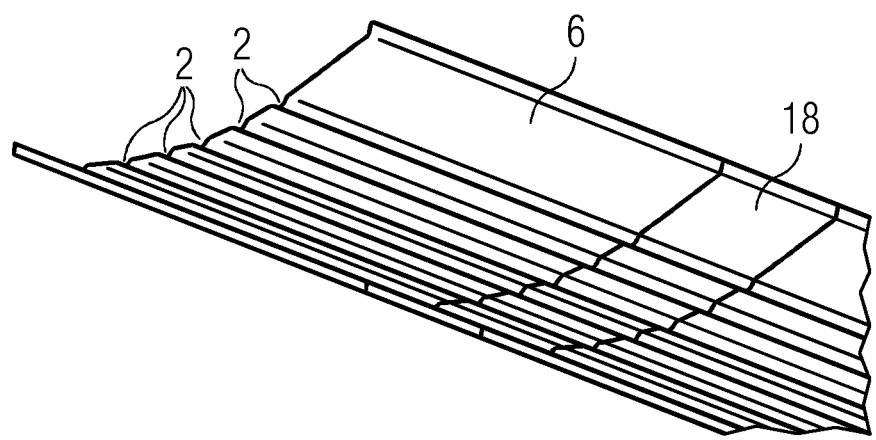
FIG. 10 depicts an example of a partial view of a single-shell couch panel with a reinforcement.

FIG. 10 depicts a partial view of a single-shell couch panel 6 with beads 2, wherein the profile of the couch panel 6 is reinforced in some regions with a reinforcement 18 in order to compensate for stress peaks in highly stressed longitudinal sections and in order to reduce the bending under the load that is exerted by the object. The reinforcement is provided, for example, by additional layers of fiber material. Since the highest stress lies in the area of the rollers 16 (e.g., supporting and guiding rollers) at the transition to the unsupported part of the couch panel 6, a reinforcement may be introduced here without, for example, adversely affecting the radioparency in the scan region.

It is to be understood that the elements and features recited in the appended claims may be combined in different ways to produce new claims that likewise fall within the scope of the present invention. Thus, whereas the dependent claims appended below depend from only a single independent or dependent claim, it is to be understood that these dependent claims may, alternatively, be made to depend in the alternative from any preceding or following claim, whether independent or dependent, and that such new combinations are to be understood as forming a part of the present specification.

While the present invention has been described above by reference to various embodiments, it may be understood that many changes and modifications may be made to the described embodiments. It is therefore intended that the foregoing description be regarded as illustrative rather than limiting, and that it be understood that all equivalents and/or combinations of embodiments are intended to be included in this description.

Although the invention has been illustrated and described in detail on the basis of the illustrative embodiments, the invention is not limited by the disclosed examples, and other variations, particularly for non-medical uses, may be derived from these by a person skilled in the art, without departing from the scope of protection of the invention.

The invention claimed is:

1. A couch panel for a patient couch for medical imaging, the couch panel comprising:
  a single-shell design;
  a plurality of beads positioned in a longitudinal direction of the couch panel and extending from a first edge to an opposite second edge along a longitudinal length of the couch panel, wherein a number and shape of the beads are configured such that the couch panel has a predefinable geometric moment of inertia, wherein each bead of the plurality of beads has a semi-circular shape curved concavely in relation to a surface of the couch panel configured to support an examination object; and two longitudinally extending edges of the couch panel bent upward with respect to the remaining couch panel, wherein each edge is not oriented in a direction of the examination object on the couch panel, wherein a portion of the couch panel having the plurality of beads is curved concavely in a transverse direction perpendicular to the longitudinal direction, wherein the semi-circular shapes of the plurality of beads, the concave curvature of the portion of the couch panel, and orientations of the edges are configured to reduce or avoid x-ray artifacts during an imaging of the examination object, and wherein the plurality of beads run from a first edge to an opposite edge along the longitudinal length of the couch panel.

2. The couch panel as claimed in claim 1, wherein the couch panel is made from a fiber-reinforced plastic.

3. The couch panel as claimed in claim 1, wherein the couch panel is made from a carbon fiber-reinforced plastic.

4. The couch panel as claimed in claim 3, wherein a wall thickness of the couch panel is 2 to 5 mm.

5. The couch panel as claimed in claim 4, further comprising:
at least one layer of a fiber material configured to locally increase the geometric moment of inertia, wherein the at least one layer is disposed in an area of the couch panel extending in the direction perpendicular to the longitudinal direction of the plurality of beads of the couch panel.

6. The couch panel as claimed in claim 1, wherein a wall thickness of the couch panel is 2 to 5 mm.

7. The couch panel as claimed in claim 1, further comprising:
at least one layer of a fiber material configured to locally increase the geometric moment of inertia, wherein the at least one layer is disposed in an area of the couch panel extending in the direction perpendicular to the longitudinal direction of the plurality of beads of the couch panel.

8. A system for medical imaging, the system comprising:
a couch panel comprising:
a single-shell design;
a plurality of beads positioned in a longitudinal direction of the couch panel, wherein a number and shape of the plurality of beads are configured such that the couch panel has a predefinable geometric moment of inertia, wherein each bead of the plurality of beads has a semi-circular shape curved concavely in relation to a surface of the couch panel configured to support an examination object; and two longitudinally extending edges of the couch panel bent upward with respect to the remaining couch panel, wherein each edge is not oriented in a direction of the examination object on the couch panel, wherein a portion of the couch panel having the plurality of beads is curved concavely in a transverse direction perpendicular to the longitudinal direction, and wherein the semi-circular shapes of the plurality of beads, the concave curvature of the portion of the couch panel, and orientations of the edges are configured to reduce or avoid x-ray artifacts during an imaging of the examination object;

at least two rollers abutting at least two beads of the plurality of beads, wherein each roller of the at least two rollers has a semi-circular shape curved convexly in relation to the surface of the couch panel, wherein each roller of the at least two rollers is configured to receive the concave curvature of a respective bead of the at least two beads, and wherein the at least two rollers are configured to guide and support the couch panel on the at least two beads during movement of the couch panel in the longitudinal direction;

a pedestal; and a linear carriage arranged movably on the pedestal and on which the couch panel is secured.

9. The system as claimed in claim 8, further comprising:
an accessory holding unit arranged on one end of the couch panel, wherein the accessory holding unit is fixed in the beads by holding rods of the accessory holding unit or is configured to a profile of the couch panel.

10. The system of claim 8, further comprising:
an X-ray imaging device configured to provide X-rays for the medical imaging of the examination object.

11. The system of claim 8, further comprising:
a computed tomography apparatus configured to provide X-rays for the medical imaging of the examination object.

12. The system of claim 8, wherein the plurality of beads run from a first edge to an opposite edge along a longitudinal length of the couch panel.

* * * * *